(12) United States Patent
Huang et al.

(10) Patent No.: US 10,112,881 B2
(45) Date of Patent: Oct. 30, 2018

(54) SKIN LIGHTENING COMPOUNDS

(71) Applicant: WiSys Technology Foundation, Inc., Madison, WI (US)

(72) Inventors: Cheng-Chen Huang, Prescott, WI (US); Aaron P. Monte, La Crosse, WI (US)

(73) Assignee: WISYS TECHNOLOGY FOUNDATION, INC., Madison, WI (US)

( * ) Notice: Subject to any disclaimer, the term of this patent is extended or adjusted under 35 U.S.C. 154(b) by 0 days.

(21) Appl. No.: 15/327,721

(22) PCT Filed: Jul. 21, 2015

(86) PCT No.: PCT/US2015/041329
§ 371 (c)(1),
(2) Date: Jan. 20, 2017

(87) PCT Pub. No.: WO2016/014529
PCT Pub. Date: Jan. 28, 2016

(65) Prior Publication Data
US 2017/0197897 A1    Jul. 13, 2017

Related U.S. Application Data (60) Provisional application No. 62/026,920, filed on Jul. 21, 2014.

(51) Int. Cl.
*C07C 43/23* (2006.01)
*A61Q 19/02* (2006.01)
*A61K 8/34* (2006.01)

(52) U.S. Cl.
CPC ............ *C07C 43/23* (2013.01); *A61K 8/347* (2013.01); *A61Q 19/02* (2013.01)

(58) Field of Classification Search
CPC .......... C07C 43/23; A61K 8/347; A61Q 19/02
See application file for complete search history.

(56) References Cited

U.S. PATENT DOCUMENTS

| 8,530,512 B2 * | 9/2013 | Monte ................ A61K 31/085 514/438 |
| 2010/0240767 A1 | 9/2010 | Majeed et al. |
| 2010/0247587 A1 | 9/2010 | Puche et al. |

OTHER PUBLICATIONS

Lee et al., Journal of Enzyme Inhibition and Medicinal Chemistry, 31: 1-13 (Year: 2015).*
Choi et al., Ann Dermatol, 24: 90-93 (Year: 2012).*

* cited by examiner

*Primary Examiner* — Johann R Richter
*Assistant Examiner* — Genevieve S Alley
(74) *Attorney, Agent, or Firm* — Boyle Fredrickson, S.C.

(57) ABSTRACT

The present invention provides a compound of Formula I,

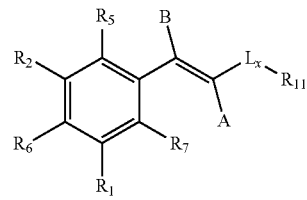

wherein $R_1$ is not H when $R_2$ is H and $R_2$ is not H when $R_1$ is H, further wherein $R_1$ is $C_nH_{(2n+1)}O$, wherein n is 1-10, $R_2$ is OH or $C_nH_{(2n+1)}O$, wherein n is 1-10, A, B and $R_1$, $R_2$, $R_5$, $R_6$, and $R_7$ are separately and independently selected from a group consisting of H, alkyl, hydroxyl, halo, nitro and aryl groups, $R_{11}$ is an alkyl or an aryl group and L is an optional linker or linking group, with x=0 or 1, i.e., if x=0, no linking group is present, or a salt or prodrug or derivative thereof that is a skin-lightening agent useful for the inhibition of melanin synthesis and/or the removal of existing melanin to function as a skin-lightening agent.

5 Claims, 8 Drawing Sheets

FIG. 1

SKIN LIGHTENING EFFICACY OF A11 ANALOGS

| ANALOG | PIGMENTATION | ANALOG | PIGMENTATION |
|---|---|---|---|
| A1 | 80% | SK0501 | 0% |
| A3 | 80% | SK0502 | 0% |
| A4 | 100% | SK0503 | 0% |
| A5 | 95% | SK0504 | 0% |
| A7 | 70% | SK0514 | 100% |
| A6, A10 | 50% | SK0515 | 60% |
| A8 | 10% | SK0516 | 10% |
| A9 | 10% | SK0517 | 60% |
| A11 | 10% | | |
| | | SK0677 | 40% |
| CL1 | 0% (40 uM) | SK0678 | 80% |
| CL2 | 5% | SK0679 | 80% |
| CL3 | 20% (40 uM) | SK0680 | 60% |
| CL4 | 0% | | |
| CL5 | 100% (40 uM) | SK0901 | 90% |
| CL6 | 0% | SK0910 | 90% |
| | | SK0951 | 0% |
| SK0222 (0422?) | 60% | SK0953 | 0% |
| SK0338F2 | 80% | SK0954 | 0% |
| SK0357F2 | 70% | | |
| SK0361 | 30% | VI072209-01 | 70% |
| SK0379 | 90% | VI072309-02 | 0% |
| SK0381 | 100% | | |
| SK0392 | 20% (50 uM) | CL1D | 80% |
| | | CL2D | 80% |
| SK0402 | 20% | | |
| SK0403 | 35% | SK0456 | 60% |
| SK0408 | 50% | SK0457 | 90% |
| SK0422 | 35% | SK0459F1 | 50% |
| SK0423 | 50% | SK0472 | 50% |
| SK0448 | 50% | SK0473 | 5% |
| SK0448F1 | 20% | SK0476 | 80% |
| SK0450 | 50% | SK0489 | 70% |

FIG. 2

REDUCTION OF EXISTING PIGMENT BY SKIN LIGHTENING COMPOUNDS
48-68hpf

FIG. 3

PIGMENT RECOVERY AFTER CHEMICAL WITHDRAWAL

REDUCTION OF MELANOCYTE PRECURSOR CELLS BY A11

SKIN LIGHTENING COMPOUNDS

CROSS-REFERENCE TO RELATED APPLICATIONS

This application claims priority from U.S. Provisional Patent Application Ser. No. 62/026,920, filed on Jul. 21, 2014, the entirety of which is expressly incorporated by reference herein.

FIELD OF THE INVENTION

The present invention relates generally to a compounds for affecting the skin, and more specifically to compounds for lightening the pigment of skin.

BACKGROUND OF THE INVENTION

Skin lightening has been a major practice in cosmetic industry. It interests many due to the ability to correct uneven skin pigment, treat pigmentation disorders, such as melasma, and provide an avenue to lighten natural skin pigmentation, which is thought to be aesthetically pleasing in a variety of cultures. For instance, in Asia the fastest growing markets include skin-lightening as it brings in billions of dollars annually. Current treatment options include chemicals (Smit et al., 2009), laser, and cryosurgery. While chemicals often are the simplest and most affordable treatment option, many chemicals are found to have adverse health effects.

However, many chemicals presently used in skin lightening exhibit adverse health effects including skin sensitivity, and cancers such as leukemia. For example, hydroquinone is a strong inhibitor of melanin (black pigment) production but was banned in Europe because of its link to leukemia and other cancer risks. Arbutin is a natural source of hydroquinone present in the leaf extracts of many kinds of berries. However, although natural, the safety of arbutin has not been well documented and the supply of arbutin is limited. Tretinoin, another proven effective skin whitener, conversely may lead to darkened skin pigmentation after time, and increases skin sensitivity to UVA and UVB rays. Other substitutes such as azelaic acid and vitamin C have limited lightening abilities and the effects diminish after a period of time.

Thus, it is desirable to develop new skin lightening chemicals that act in different mechanistic pathways than the present therapeutic options in hopes of developing safer skin-lightening alternatives.

SUMMARY OF THE INVENTION

According to one aspect of the present invention, the present invention provides a compound of Formula I, II or III or a salt or prodrug or derivatives thereof, including but not limited to ether derivatives, acid derivatives, amide derivatives, ester derivatives and the like. Generally, the compound, salt or prodrug is a skin-lightening agent useful for the inhibition of melanin synthesis and/or the removal of existing melanin to function as a skin-lightening agent.

According to an exemplary embodiment of the present invention, the present invention provides skin lightening compound of Formula I, or a salt or prodrug useful for inhibiting melanin synthesis and removal of existing melanin pigmentation. Formula I is shown as follows:

wherein:

$R_1$ is not H when $R_2$ is H and $R_2$ is not H when $R_1$ is H, further wherein $R_1$ is $CH_{(2n+1)}O$, wherein n is 1-10;

$R_2$ is OH or $CH_{(2n+1)}O$, wherein n is 1-10;

A, B and $R_1$, $R_2$, $R_5$, $R_6$, and $R_7$ are separately and independently selected from a group consisting of H, alkyl, hydroxyl, halo, nitro and aryl groups;

$R_{11}$ is an alkyl or an aryl group; and

L is an optional linker or linking group, with x=0 or 1, i.e., if x=0, no linking group is present.

As is noted, "L" is an optional linking group. Various suitable linking groups will be suggested to one skilled in this art in view of this disclosure. "L" is preferably a chalcogen, more preferably O, or S. "L" can also be, essentially, a divalent linking structure known to the art. For example, "L" can be —$CH_2$—, lower alkyl, amino e.g., —NH—, —NR— where R is lower alkyl, and —$CF_2$— among many others.

According to another exemplary embodiment of the present invention, the skin lightening compound, salt or prodrug is according to Formula II:

Formula (II)

wherein:

$R_1$ is not H when $R_2$ is H and $R_2$ is not H when $R_1$ is H, further wherein $R_1$ is $CH_{(2n+1)}O$, wherein n is 1-10;

$R_2$ is OH or $CH_{(2n+1)}O$, where n is 1-10;

A, B and $R_3$ through $R_{10}$ are separately and independently selected from a group consisting of H, alkyl, hydroxyl, halo, nitro and aryl groups; and L is an optional linker or divalent linking group, with x=0 or 1, i.e., if x=0, no linking group is present.

In a preferred embodiment, $R_1$ is $CH_3O$, $R_2$ is OH or $CH_{(2n+1)}O$, where n is 1-10; and A, B and $R_3$ through $R_{10}$ are independently selected from a group consisting of H, alkyl and aryl groups.

In another preferred embodiment, $R_1$ is $CH_3O$, $R_2$ is OH and A, B and $R_3$ through R.sub.10 are independently selected from a group consisting of H, alkyl and aryl groups.

In another exemplary aspect of the present invention the skin lightening compound is according to Formula III:

Formula III wherein:

$R_1$ is not H when $R_2$ is H and $R_2$ is not H when $R_1$ is H, further wherein $R_1$ is OH or $CH_{(2n+1)}O$, wherein n is 1-10;

$R_2$ is OH or $CH_{(2n+1)}O$, where n is 1-10;

W is alkyl, phenyl, halophenyl, pyridyl, piperidyl, or a substituted or unsubstituted aryl group, including certain unsubstituted and substituted aromatic heterocycles; and L is a linker or linking group selected from O, S, NH, $CF_2$, or $CH_2$, and x=0 or 1, i.e., if x=0, no linking group is present. The term "aryl" herein is to be broadly understood as is described below.

Yet another aspect of the present invention describes a method of lightening the skin in a subject in need thereof, said method comprising the step of administering an effective amount of a compound having a structure represented by Formulas I, II or III or a salt or prodrug thereof.

Another aspect of the invention provides a pharmaceutical composition, comprising: (a) an effective amount of a compound having a chemical structure represented by Formula I, II or III, or a salt or a prodrug thereof; and (b) a pharmaceutically-acceptable carrier. The compound, salt or prodrug is a skin-lightening agent.

Yet another aspect of the invention provides a method of inhibiting melanin synthesis and/or removing existing pigment in the skin. The method comprising contacting the skin in which melanin synthesis is to be inhibited or pigment removed with a melanin inhibiting or pigment removing amount of a compound according to Formula I, II or III, or salt or prodrug thereof.

Another aspect of the invention provides a composition suitable for inhibiting melanin synthesis and/or removing existing melanin in the skin. The composition comprises: a first ingredient which inhibits melanin synthesis and/or removes existing melanin in the skin comprising the compound, prodrug or salt of claim 1; and a second ingredient which comprises an acceptable carrier or an article of manufacture. In one embodiment, the acceptable carrier is a pharmaceutically acceptable carrier, an antibacterial agent, a skin conditioning agent, a lubricating agent, a coloring agent, a moisturizing agent, binding and anti-cracking agent, a perfuming agent, a brightening agent, a UV absorbing agent, a lightening agent, a transparency imparting agent, a thixotropic agent, a solubilizing agent, an abrasive agent, an antioxidant, a skin healing agent, a cream, a lotion, an ointment, a shampoo, an emollient, a patch a gel or a sol. In another embodiment, the article of manufacture is a textile, a fiber, a glove or a mask.

Numerous other aspects, features, and advantages of the present invention will be made apparent from the following detailed description together with the drawings figures.

BRIEF DESCRIPTION OF THE DRAWINGS

The drawings illustrate the best mode currently contemplated of practicing the present invention.

In the drawings:

FIG. 1 are photographs of the inhibition of pigment formation by skin-lightening compounds. Zebrafish embryos were incubated in compounds from 24 hpf (hours post fertilization) to 72 hpf. The compounds currently used in cosmetic products are kojic acid, arbutin, niacinamide, tretinoin, and gallic acid showed different degrees of pigment inhibition. Several not-on-market compounds (in red) were tested and show strong pigment inhibition. Note that niacinamide, tretinoid, and phenoxidiol (or phe in later figures) clearly showed abnormalities to developing embryos, such as the curvy body by niacinamide.

FIG. 2 is a table of the skin lightening efficacy of A11 analogs. Approximately 54 A11 analogs have been synthesized and we tested them on normal finish embryo. About 28 of them still maintain pigment reduction by 50% (highlighted).

FIG. 4 are photographs of the pigment recovery after chemical withdrawal. Zebrafish embryos were treated with skin lightening compounds from 24-72 hpf followed by several washes to remove the compounds then incubated in 1120. Twenty four hours after wash, the embryos were imaged. It is clear that the pigment recovers within 24 hours in many cases, but not so in A11, Phe, PTU-treated embryos. MoTP-treated embryos also showed limited recovery (not shown).

FIG. 5 is a schematic view of the melanin biosynthesis pathway. There are two major types of melanin, eumelanin (brown and black pigment) or Pheomelanin (yellow, orange, and red pigment). The starting material for all the melanin is L-tyrosine which is first turned into DOPA and then DOPA-quinone by the same enzyme called tyrosinase. Thus tyrosinase is believed to be the key enzyme of melanin synthesis.

FIG. 6 is a graph illustrating the results of in vitro assay for various tyrosinase inhibitors. The assay is set up by mixing purified tyrosinase from mushroom with L-tyrosine with or without test chemical. Active tyrosinase will turn L-tyrosine into DOPAchrome which is orange color. The absorbance at 490 nm which reflects the amount of DOP-Achrome and thus the tyrosinase activity was taken at 20', 60' and 120' of reaction. While the known tyrosinase inhibitors, PTU, kojic acid and artbutin show strong inhibition, A11 and two of the A11 analogs, SK0392 and CLS, show no inhibition at all. More than 50 A11 analogs have been tested with this assay and none of them show tyrosinase inhibition (not shown). Interestingly, MoTP and GA (gallic acid) show enhancement of tyrosinase activity with still unknown mechanism.

FIG. 10 are photographs of A11 and other compounds effects on melanoma-forming fish. The transgenic zebrafish TG (kit:ras) embryos exhibit overproliferation of melanocytes starting from 2 days post fertilization. Using the transgenic embryos, we found that A11 seems to significantly inhibit the melanocyte overproliferation comparing the 24-96 hpf A11-treated embryos with the control. When A11 was given to 48 hpf embryos in which over-proliferated melanocytes are readily apparent, A11-treated embryos show near normal level of melanocytes after 48 hours of treatment, suggesting that A11 might inhibit the melanocyte development and/or proliferation and survival.

FIGS. 11A-11D are graphs of A11 effects on mammalian melanoma cells. Mouse melanoma cell line B16-F10 is a commonly used mammalian cells for melanogenesis and melanocyte studies. When examine the cell proliferation (blue bars), we found that 40 uM A11 can significantly inhibit the melanocyte proliferation as well as arbutin at 100 mM, kojic acid, and. MoTP. Other human skin lightening compounds have no or minimal effect on melanocyte proliferation. Melanin synthesis (green bars) in mouse melanoma cell is also reduced by 40 uM A11 and most of the skin lightening compounds but not MEK-I or niacinamide. The two graphs on top are cell number per 0.5 cubic mm. The Y axis in the lower two graphs is absorbance of 490 nm visible light by melanin. Higher absorbance means more melanin.

DETAILED DESCRIPTION OF THE INVENTION

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a compound" includes a plurality of such compounds and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, the term "isomer" includes, but is not limited to stereoisomers and analogs, structural isomers and analogs, conformational isomers and analogs, and the like. In one embodiment, this invention encompasses the use of different stereoisomers of skin lightening compound(s) of Formula I, II or III. It will be appreciated by those skilled in the art that the skin lightening compound(s) useful in the present invention may contain a chiral center. Accordingly, the compounds used in the methods of the present invention may exist in, and be isolated in, optically-active or racemic forms. Some compounds may also exhibit polymorphism. It is to be understood that the present invention encompasses the use of any racemic, optically-active, polymorphic, or stereoisomeric form, or mixtures thereof, which form possesses properties useful in the treatment of melanin and/or pigmentation conditions described and claimed herein. In one embodiment, the skin lightening compound(s) are the pure (Z) or (E)-isomers. In another embodiment, the skin lightening compound(s) are the pure (R) or (S)-isomers. In another embodiment, the compounds are a mixture of the (R) and the (S) isomers or (E) and (Z) isomers. In another embodiment, the compounds are a racemic mixture comprising an equal amount of the (R) and the (S) isomers. Furthermore, where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention. Preparation of these isomers, compounds and derivatives are well known to one of ordinary skill in the art.

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Pharmaceutically acceptable salts for topical administration to body surfaces using, for example, creams, gels, drops, and the like, include the skin lightening compound(s) or their physiologically tolerated derivatives such as salts, esters, N-oxides, and the like are prepared and applied as solutions, suspensions, or emulsions in a physiologically acceptable diluent with or without a pharmaceutical carrier.

This invention further includes methods utilizing derivatives of the skin lightening compound(s). The term "derivatives" includes but is not limited to ether derivatives, acid derivatives, amide derivatives, ester derivatives and the like. In addition, this invention further includes methods utilizing hydrates of the skin lightening compound(s). The term "hydrate" includes but is not limited to hemihydrate, monohydrate, dihydrate, trihydrate and the like.

This invention further includes methods of utilizing metabolites of the skin lightening compound(s). The term "metabolite" means any substance produced from another substance by metabolism or a metabolic process.

The present invention includes within its scope prodrugs of the skin lightening compound(s). In general, such prodrugs will be functional derivatives of the compound of Formula I which are readily convertible in vivo into the required compound of Formula I, II or III. Conventional procedures for the selection and preparation of suitable prodrug derivatives are described, for example, in Design of Prodrugs, ed. H. Bundgaard, Elsevier, 1985.

As defined herein, "contacting" means that the skin lightening compound(s) used in the present invention is introduced into a sample containing the receptor in a test tube, flask, tissue culture, chip, array, plate, microplate, capillary, or the like, and incubated at a temperature and time sufficient to permit binding of the skin lightening compounds to a receptor. Methods for contacting the samples with the skin lightening compounds or other specific binding components are known to those skilled in the art and may be selected depending on the type of assay protocol to be run. Incubation methods are also standard and are known to those skilled in the art.

In another embodiment, the term "contacting" means that the skin lightening compound(s) used in the present invention is introduced into a subject receiving treatment, and the compound is allowed to come in contact in vivo. In yet another embodiment, "contacting" includes topical application of the skin lightening compound(s) on a subject.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

In the treatment, the skin lightening compounds(s) may be administered in any suitable manner, such as on a regimen of 1 to 4 times per day, or on a continuous basis via, for example, the use of a transdermal patch.

As used herein, the term "administering" refers to bringing a patient, tissue, organ or cells in contact with skin lightening compounds according to Formulas I, II or III. As used herein, administration can be accomplished in vitro, i.e. in a test tube, or in vivo, i.e. in cells or tissues of living organisms, for example, humans. In certain embodiments, the present invention encompasses administering the compounds useful in the present invention to a patient or subject. A "patient" or "subject", used equivalently herein, refers to a mammal, preferably a human or an animal, that: (1) has a melanin or pigmentation condition remediable or treatable by administration of the skin lightening compound(s) according to Formula I, II or III; or (2) is susceptible to a melanin or pigmentation condition that is preventable by administering the skin lightening compound(s) according to Formula I, II or III.

In yet another method according to the invention, a pharmaceutical composition can be administered in a controlled release system. For example, the agent may be delivered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In yet another embodiment, polymeric materials can be used. In yet another embodiment, a controlled release system can be placed in proximity to the therapeutic target, i.e., the skin, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially intrathecally, sublingually, rectally, vaginally, nasally, by inhalation, cutaneously, topically and systemically.

The pharmaceutical preparations administrable by the invention can be prepared by known dissolving, mixing, granulating, or tablet-forming processes. For oral administration, the anti-infective compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the anti-infective compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage from affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, "pharmaceutical composition" means therapeutically effective amounts of the skin lightening compound(s) together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of melanin or pigmentation development; and (b) the reversal or stabilization of melanin or pigmentation development. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

The liquid forms in which the pharmaceutical compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. Thus for example, in a preferred example, liquid form of the novel composition will include oral rinse solutions, anti-caries solutions, disinfectant solutions, and other liquids forms well known to one of ordinary skill in the art.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

Other embodiments of the compositions administered according to the invention incorporate particulate forms, protective coatings, protease inhibitors or permeation enhancers for various routes of administration, including parenteral, pulmonary, nasal and oral.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N. Y., pp. 353-365 (1989); Lopez-Berestein ibid., pp. 317-327; see generally ibid).

The pharmaceutical preparation can comprise the skin lightening compound alone, or can further include a pharmaceutically acceptable carrier, and can be in solid or liquid form such as tablets, powders, capsules, pellets, solutions, suspensions elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the skin lightening compound can be administered to a subject by, for example, subcutaneous implantation of a pellet. In a further embodiment, a pellet provides for controlled release of a skin lightening compound over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Pharmaceutically acceptable parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Pharmaceutically acceptable carriers for controlled or sustained release compositions administrable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Pharmaceutically acceptable carriers include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; and Katre et al., 1987). Such modifications may also increase the compounds solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Preferred Exemplary Embodiments

The inventors have found a compound that shows efficacy in skin lightening by inhibiting the formation of melanin pigmentation and reducing existing melanin pigmentation in zebrafish embryos and cultured mouse melanocytes.

Accordingly, the present invention provides skin lightening compound of Formula I, or a salt or prodrug useful for inhibiting pigment formation and reduction of existing melanin pigmentation. Formula I is shown as follows:

Formula I wherein:

$R_1$ is not H when $R_2$ is H and $R_2$ is not H when $R_1$ is H, further wherein $R_1$ is $CH_{(2n+1)}O$, wherein n is 1-10;

$R_2$ is OH or $CH_{(2n+1)}O$, wherein n is 1-10;

A, B and $R_1$, $R_2$, $R_5$, $R_6$, and $R_7$ are separately and independently selected from a group consisting of H, alkyl and aryl groups;

$R_{11}$ is an alkyl or an aryl group; and

L is an optional linker or linking group, with x=0 or 1, i.e., if x=0, no linking group is present.

As is noted, "L" is an optional linking group. Various suitable linking groups will be suggested to one skilled in this art in view of this disclosure. "L" is preferably a chalcogen, more preferably O, or S. "L" can also be, essentially, a divalent linking structure known to the art. For example, "L" can be —$CH_2$—, lower alkyl, amino e.g., —NH—, —NR— where R is lower alkyl, and —$CF_2$— among many others.

In one exemplary embodiment, the skin lightening compound, salt or prodrug is according to Formula II:

Formula (II)

wherein:

$R_1$ is not H when $R_2$ is H and $R_2$ is not H when $R_1$ is H, further wherein $R_1$ is $CH_{(2n+1)}O$, wherein n is 1-10;

$R_2$ is OH or $CH_{(2n+1)}O$, where n is 1-10;

A, B and $R_3$ through $R_{10}$ are separately and independently selected from a group consisting of H, alkyl and aryl groups; and L is an optional linker or divalent linking group, with x=0 or 1, i.e., if x=0, no linking group is present.

In one exemplary embodiment, $R_1$ is $CH_3O$, $R_2$ is OH or $CH_{(2n+1)}O$, where n is 1-10; and A, B and $R_3$ through $R_{10}$ are independently selected from a group consisting of H, alkyl and aryl groups.

In another exemplary embodiment, $R_1$ is $CH_3O$, $R_2$ is OH and A, B and $R_3$ through R.sub.10 are independently selected from a group consisting of H, alkyl and aryl groups.

In another exemplary embodiment, said skin lightening compound, salt or prodrug is shown in Formula III as follows:

Formula (III)

or salt and prodrug thereof, wherein:

$R_1$ is not H when $R_2$ is H and $R_2$ is not H when $R_1$ is H, further wherein $R_1$ is $CH_{(2n+1)}O$, wherein n is 1-10;

$R_2$ is OH or $CH_{(2n+1)}O$, where n is 1-10;

W is alkyl, phenyl, halophenyl, benzothiophene, furan, indole, indazole, imidazole, piperidyl, pyridyl, pyrrole, thiazole, thiophene, or a substituted or unsubstituted aryl group, including additional other substituted and unsubstituted aromatic heterocycles.

Experimental

Several current human drugs, Arbutin, kojic acid, Niacinamide, imperatorin, gallic acid, azelaic acid and Tretinoin, and a known melanin synthesis inhibitor, phenylthiourea (PTU), and two recently reported compounds, phenoxidiol/haginin and (2-Morpholinobutyl)-4-thiophenol/MoTP, were included as a comparison in various testing protocols in comparison with the melanin synthesis effects of certain exemplary compounds of the present invention, A11 and MEK-I, with the particular compounds having the following structures:

Arbutin

Kojic acid

A11

Niacinamide

Phenoxodiol
(Haginin A)

·CH₃CH₂OH

MEK-I

Tretinoin

MoTP

Phenylthiourea
(PTU)

The testing protocols for these compounds are as follows:

a. To test the inhibition of pigment formation, the zebrafish embryos were treated with the drugs from 24 to 72 hours post-fertilization (hpf). The embryos were monitored and imaged throughout their development to track the development of melanin pigment relative to a control group to which water was administered (Protocol 1).

b. To test the effects of the drugs on existing melanin and/or melanocytes, the embryos were treated with the chemicals at 48 hpf, after pigment had developed. The embryos were again monitored and imaged throughout their development relative to a control group to which water was administered (Protocol 2).

c. Additionally, to test the ability of the pigment to recover after being treated with our drugs, all embryos were treated at 24 hpf with the chemicals until the 68 hpf or 72 hpf time period, then washed with water to remove the treatment. The embryos were again monitored and imaged throughout their development relative to a control group to which water was administered (Protocol 3).

Comparison of Skin-Lightening Compounds

The skin-lightening effect of several compounds using zebrafish embryo, including three compounds currently used in humans, namely, Arbutin, Niacinamide, Tretinoin, a known melanin synthesis inhibitor, phenylthiourea (PTU)

and the two new compounds identified by our lab A11 and MEK-I was tested using Protocol 1. The black pigment (or melanin) is very easy to observe in zebrafish. In brief, adult zebrafish are taken to breed embryos. Morphologically normal embryos of 24 hours post fertilization (hpf) stage will be selected for incubation in the drugs from 24 to 72 hours. During the incubation, the embryos are monitored and imaged (see FIG. 1) to track the development of melanin. This experiment was repeated at least three times to obtain a reproducible result. To broaden the comparison with other skin-lightening products, this project can also test other compounds, kojic acid, gallic acid, (2-Morpholinobutyl)-4-thiophenol/MoTP and Haginin/phenoxidiol. The results obtained from these experiments inform us of the skin-lightening efficacy as well as mechanistic difference between these compounds. In the meantime, the whole organism context also allows us to examine the toxicological profile, if any, of these compounds. The same protocol is also used for the experiments using the melanoma forming zebrafish.

Figure 1:
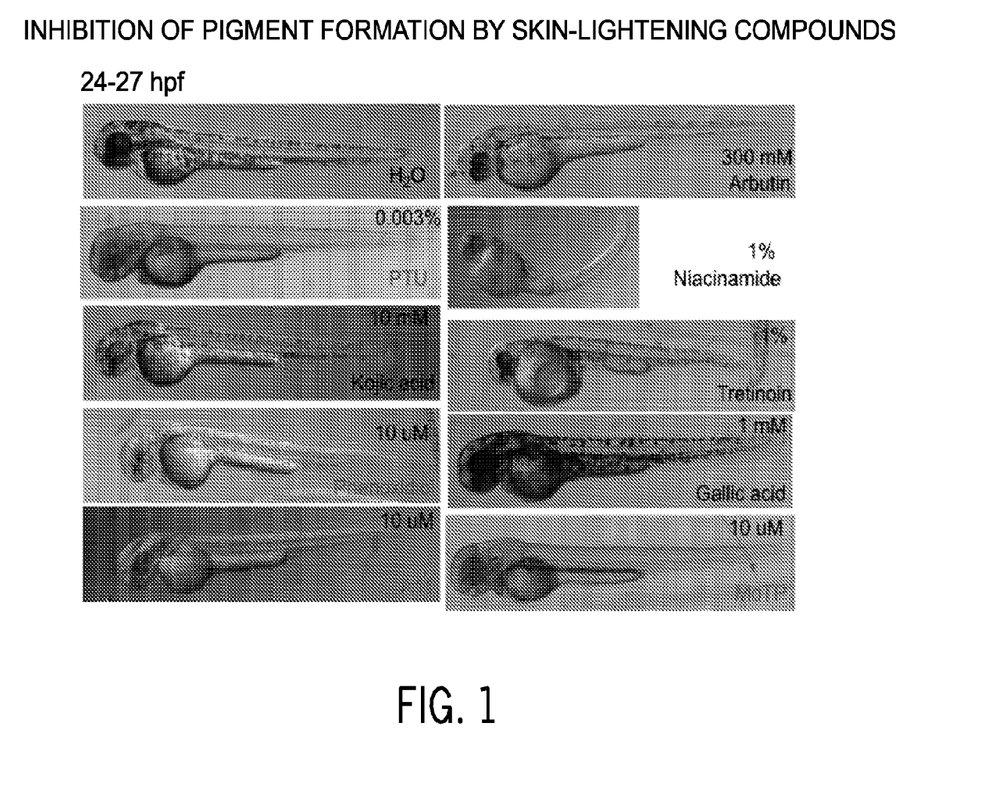
Figure 2:
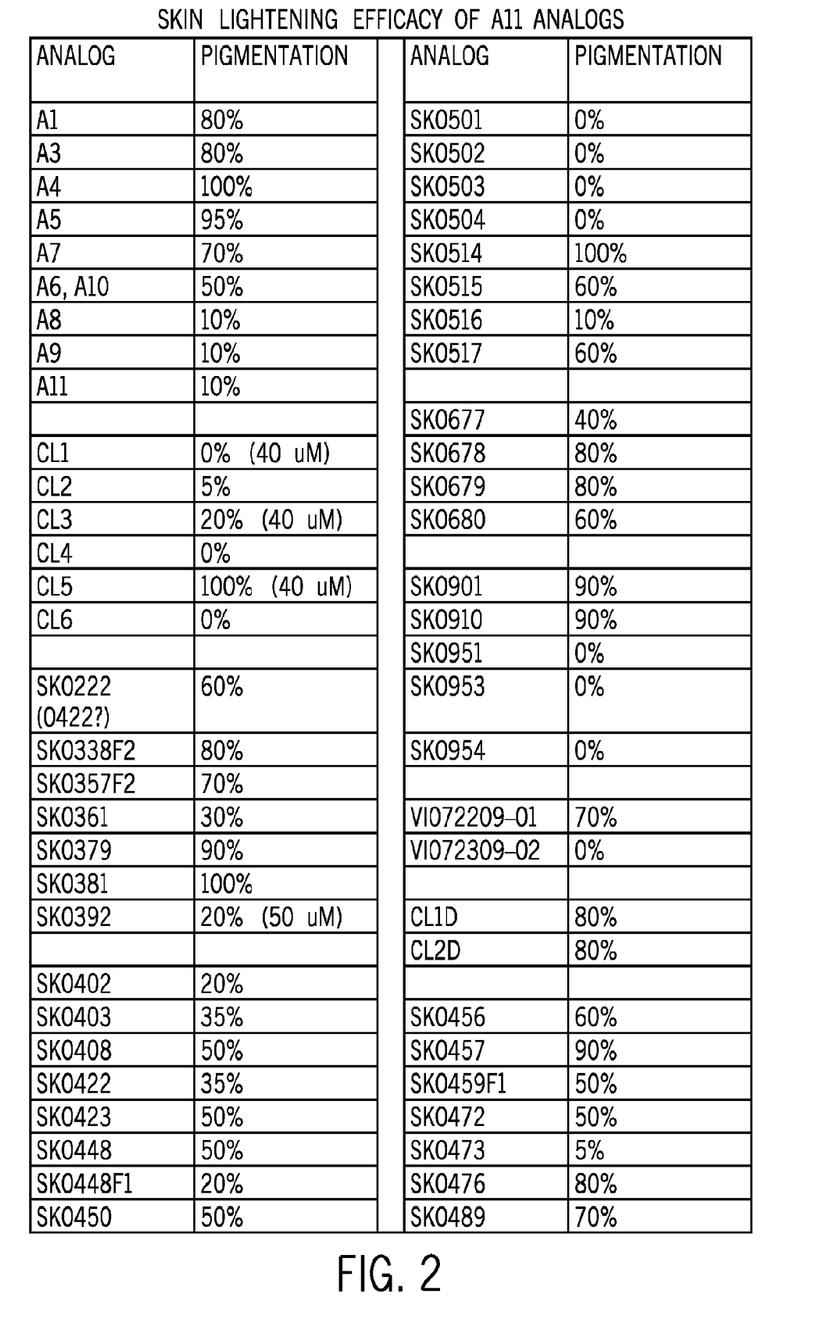

In reference to FIG. 1, the results show that:
The five human drugs work on zebrafish, pretty much as in humans.
The human drugs arbutin, niacinamide, tretinoin cause morphological toxicity.
A11, phenoxidiol, MoTP, and PTU work on zebrafish with strong pigmentation inhibition.
The overall efficacy of the skin-lightening effects of the drugs tested according to the observed results is:
PTU=phenoxidiol=A11=MoTP>Arbutin>Niacinamide>Tretinoin>kojic acid>gallic acid Many A11 analogs have been synthesized and tested as well such as those disclosed in U.S. Pat. No. 8,530,512, hereby incorporated by reference herein in its entirety. Although not as potent as A11, about 43% of the A11 analogs can still reduce pigment by more than 50% (FIG. 2).

Testing the Skin-Lightening Efficacy on Existing Pigmentation

Due to the fact that most skin-lightening compounds inhibit tyrosinase quite specifically, these compounds typically have no effect on already existing pigment and thus are slow in reducing pigment to lighten the skin color. Thus, we compared the compound effect on existing pigment using older embryos at 48 hpf. The embryos were again monitored and imaged throughout their development according to Protocol 2. As we expected, most skin-lightening compounds have no or little effect on existing pigment. Interestingly, A11 showed strong and quick pigment reduction.

Figure 3:
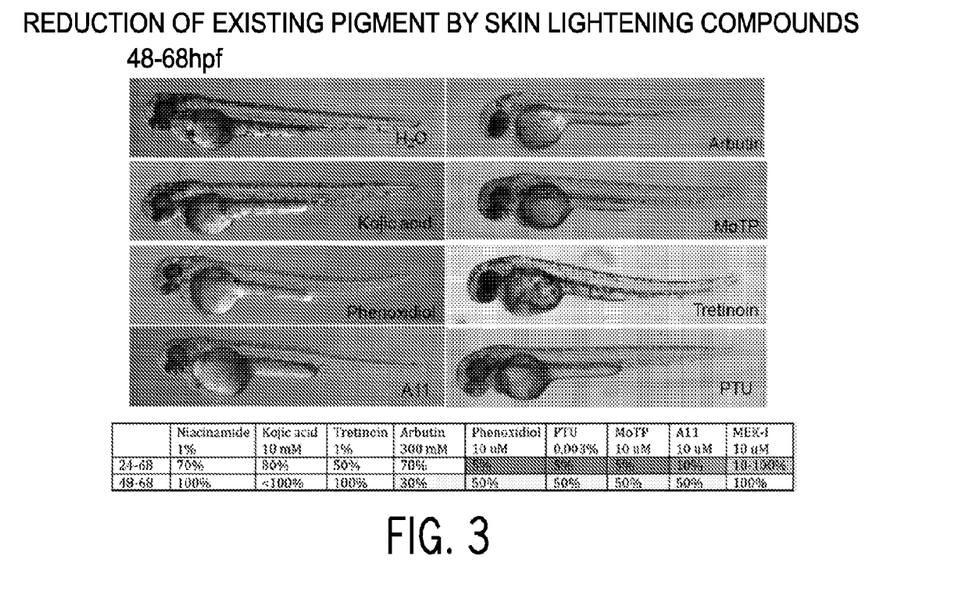
FIG. 3 are photographs and a table of the reduction of existing pigment by skin lightening compounds. Embryos were incubated in compounds from 48 hpf when some pigments already formed to 68 hpf. While most human compounds showed minimal or no pigment reduction, such as kojic acid and tretinoin, strong reduction of existing pigment was observed in A11, Phenoxidiol and MoTP treated embryos.

In reference to FIG. 3, the results show that:
A11 and phenoxidiol are strong in reducing existing pigment while PTU, MoTP, and arbutin can moderately reduce existing pigment. Other compounds show limited or no effect on existing pigment.

Testing the Skin-Lightening Efficacy After Compound Withdrawal

It has been reported that melanin usually reappears after the withdrawal of skin lightening products. We studied this question by treating fish embryos from 24-72 hpf, according to Protocol 3, to create strong pigment reduction then wash off the compounds and track the pigment recovery. Our hypothesis was that pigment will recover quickly after the withdrawal of those skin-lightening compounds that specifically inhibit tyrosinase function. Interestingly, while the pigment recovered back to near normal 24 hours after chemical withdrawal in those embryos treated with current skin-lightening compounds, the pigment recovered less than 50% in A11-treated embryos, suggesting A11 has longer pigment inhibition effect but does not remove or inhibit pigment permanently. A drug with the ability to permanently remove or inhibit pigment might pose a concern of causing vitiligo.

Figure 4:
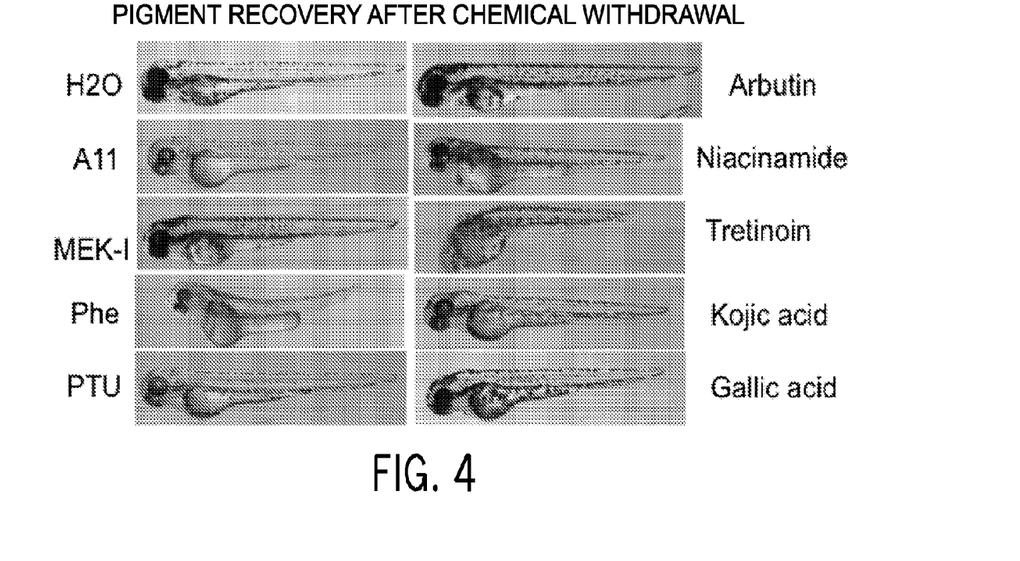

In reference to FIG. 4, the results show that:
most of the compounds tested recover completely to 100% of pigmentation within 24 hours after wash, with the exception of A11, phenoxidiol and PTU, which only recover to approximately 50% or less of pigmentation.

Molecular Mechanisms of A11 and MEK-I

Figure 5:
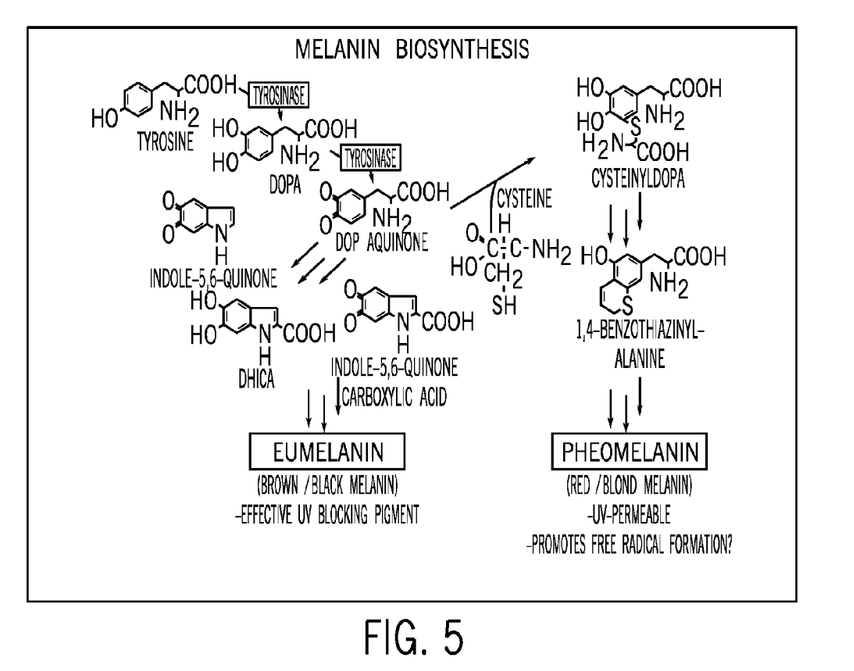
Figure 6:
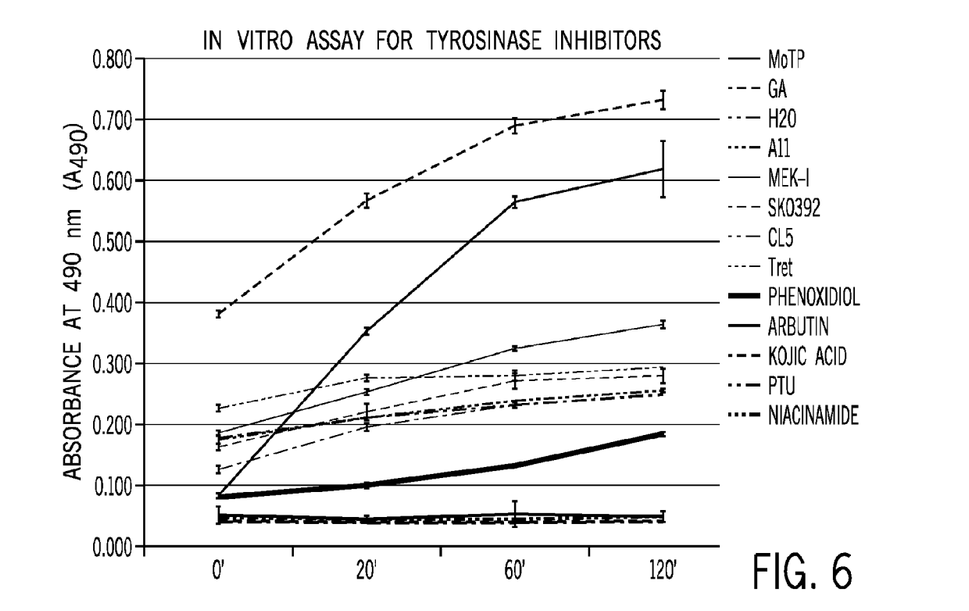

Most of the current skin-lightening compounds reduce pigment by inhibiting the melanin synthesis enzyme called tyrosinase (FIG. 5). To test whether A11 has the same mechanism, we carried out the commonly used in vitro assay to evaluate tyrosinase activity. The assay is usually done by mixing purified tyrosinase from mushroom with L-tyrosine, which is the substrate of tyrosinase, and with or without test chemical. Reaction with active tyrosinase will quickly turn L-tyrosine into a color product called dopachrome which is an intermediate product in the melanin synthesis pathway. The amount of dopachrome can be measured by a spectrophotometer at A490 nm visible light. A number of different compounds, including A11, were evaluated to determine their inhibition of tyrosinase. As shown in FIG. 6, A11 does not inhibit tyrosinase, and thus does not seem to affect melanin synthesis biochemical pathway which distinguish itself from other compounds. (The same result is also observed in almost all the A11 analogs.)

Figure 7A:
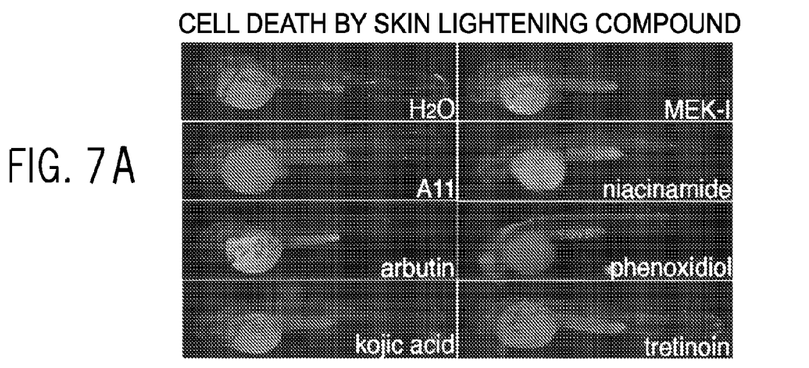
FIGS. 7A-7B are photographs and an associated graph illustrating the cell death by skin lightening compounds. Embryos treated with skin lightening compounds were fixed and processed for enzymatic labeling for apoptosis. Most skin lightening compounds don't cause significant apoptosis except for niacinamide, phenoxidiol, and tretinoin which is apparently associated with the developmental abnormalities caused by these compounds. MoTP has been shown to induce cell death in melanocytes and thus causes slight increase of apoptosis in our experiment.
Figure 7B:
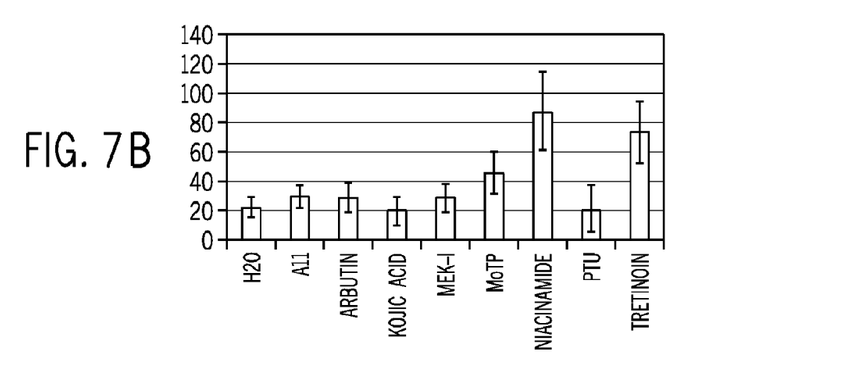

Although it is rare, one compound MoTP was reported to cause cell death specifically in melanocyte. We tested whether other skin lightening compounds can also cause melanocyte cell death. Using a fluorescence labeling assay, we were able to detect the apoptotic cells. Although we were not able to specifically identify apoptotic melanocyte due to technical difficulties, we were able to evaluate the overall cell death in the compound treated embryos. The results show that A11 cause no significant cell death than the control embryos whereas MoTP causes slightly higher level of apoptosis. Niacinamide and phenoxidiol which cause developmental defects clearly show large increase of apoptosis (FIG. 7).

Figure 8:
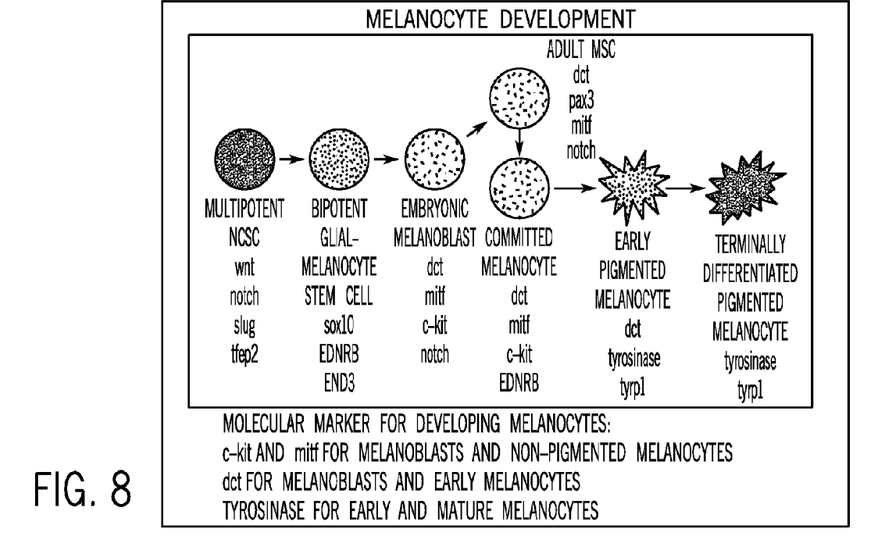
FIG. 8 is a schematic view of the genetic mechanism for melanocyte development. Genes expressed in the different stages of developing melanocytes could be used to evaluate the chemical effect on melanocyte development. For example, dct (domachrome tautomerase) is primarily expressed in the precursors of melanocyte while tyrosinae is only expressed in the mature or near mature melanocytes.

To further understand the molecular mechanism of the skin-lightening products, the expression of certain genes was examined that are involved in melanin biosynthesis and melanocyte development, including the tyrosinase gene, the starting enzyme in the melanin synthesis pathway, mit-f, a melanocyte differentiation marker, and dct gene, that is known to expressed in the mid and late stage of melanocyte development, and others (FIG. 8). The cDNA of these genes was cloned and used to generate anti-sense RNA probes.

By performing in situ hybridization with these probes, the expression of these genes was detected to determine whether the skin-lightening compounds have any role in the melanocyte development as illustrated in FIG. 8. While most human skin lightening products have been shown to inhibit tyrosinase activity (FIG. 6), to date none of them has been tested on the melanocyte development.

Figure 9A:
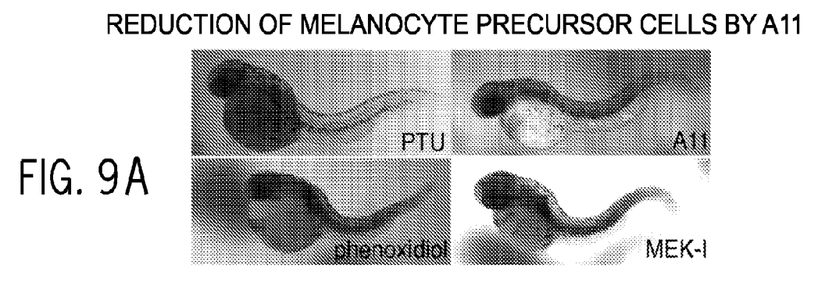
FIGS. 9A-9C are photographs and associated graphs of the reduction of melanocyte precursor cells by A11. In situ hybridization for the dct-expressing cells which are believed to be the precursor cells of melanocytes show that A11 and phenoxidiol, but not MEK-I, cause significant lower number of dct+ cells. Cell counts are shown in the middle panel. (Bottom) Quantitative PCR to measure the mRNA of dct in compound treated embryos show reduction of dct expression by A11 and phenoxidiol, supporting the results from in situ hybridization.
Figure 9B:
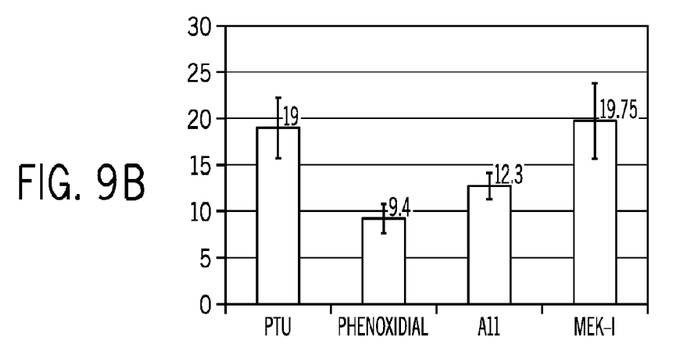
Figure 9C:
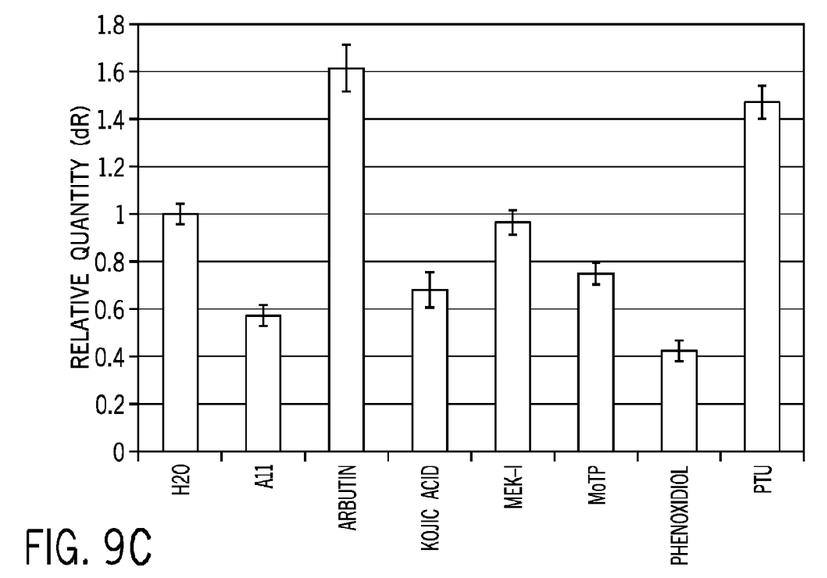

Interestingly, both A11- and phenoxidiol-treated embryos showed fewer dct-positive cells while MEK-I and PTU had no effect on the number of dct expressing cells (FIG. 9, top and middle panels). We also carried out qPCR to measure the dct mRNA expression. In consistent with the in situ hybridization result, we observed significantly lower expression of dct expression in both the A11- and phenoxidiol-treated embryos. MEK-I caused no change in dct expression. Interestingly, both arbutin and PTU caused slightly increase of dct expression.

Figure 10:
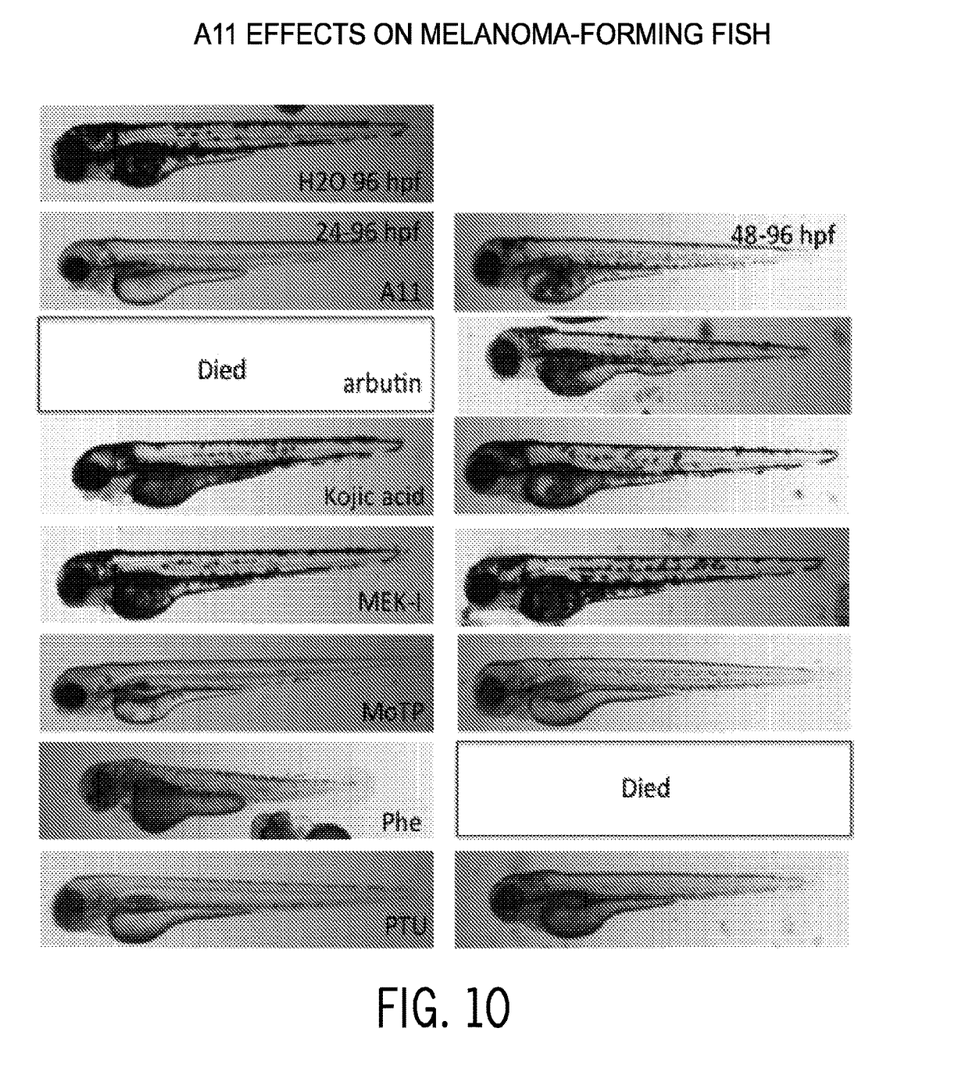
Figure 11A:
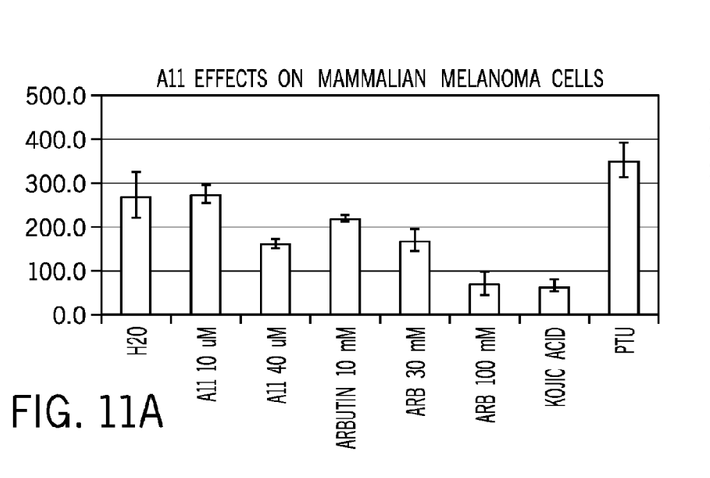
Figure 11B:
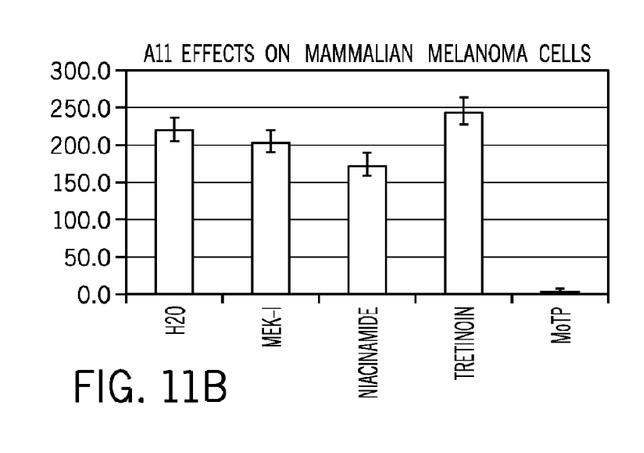
Figure 11C:
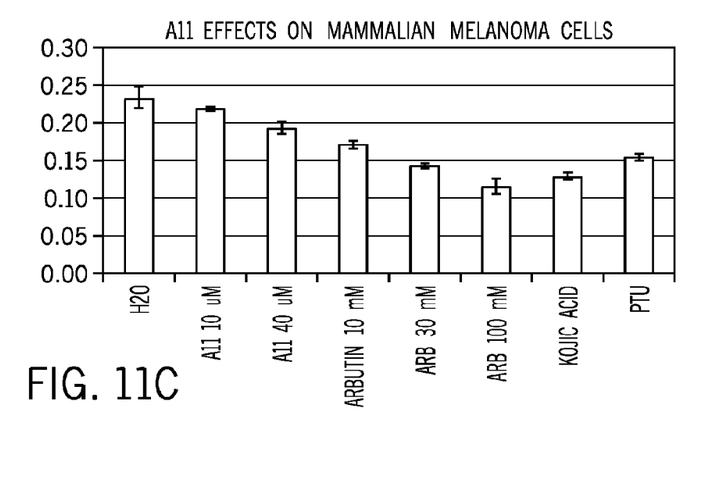
Figure 11D:
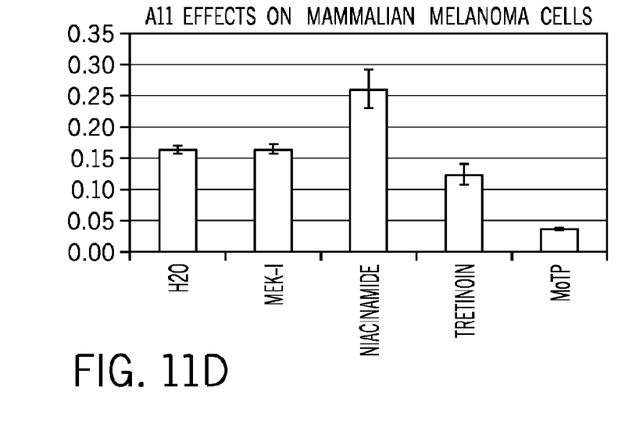

Recently, a melanoma transgenic zebrafish has been generated using the GAL4-UAS system to overexpress ras in melanocytes (Santoriello et al., 2010). In the transgenic embryos, overproliferation of melanocyte is evident as early as two days post fertilization (FIG. 10). If A11 caused pigment reduction by suppressing melanocyte development, we expect to see inhibition of melanoma formation by A11. After incubating the melanoma embryos in A11 from 24-72 hpf, we saw significant suppression of melanoma formation. The effect lasted for several days. A11 also cause reduction of pigment in older melanoma embryos, as pigment is less in the embryos treated with A11 from 48-96 hpf (FIG. 10)

A11 Causes Slight Melanin Reduction and Cell Death in Cultured Mouse Melanoma Cells So far, we have used zebrafish embryos to reveal the different mechanism and toxicity of the tested skin-lightening compounds. We seemed to see a new mechanism of A11 which is to reduce dct-expressing cells. Lastly, we used the mouse melanoma cells to test whether A11 has any effect on the differentiated mammalian melanoma cells. In this experiment, we first seeded approximately the same number of cells in each well of the 24-well plate supplied with fresh complete growth medium with different skin lightening compound. After 48 hours of incubation, we counted the cell numbers to evaluate the cell proliferation and lysed the cells from additional identically set-up wells and measured the total amount of melanin in treated melanoma. We found that A11 at 40 uM slightly inhibited the melanoma cell proliferation (FIG. 11). MEK-I, tretinoin, or PTU didn't seem to have any effect on melanocyte proliferation. Inconsistent with literature, MoTP killed all the melanoma cells. For melanogenesis, we found that arbutin, kojic acid, PTU, and tretinoin showed significant reduction of melanin in melanoma cells but A11 showed no melanin reduction at 10 uM and only slight reduction at 40 uM concentration. These results further support the notion that A11 doesn't seem to affect differentiated melanocyte very much. Instead, A11 inhibits melanocyte development to reduce pigment.

Chemical Synthesis

While testing on zebrafish embryos requires minimal amounts of compound, more A11 is needed for the subsequent assays with small mammals, e.g., guinea pigs. An efficient approach for the production of compound A11 and a number of its chemical analogs has been developed which is scalable and should allow for the preparation of the gram quantities of this agent required in this and subsequent investigations. Specifically, as shown in scheme 1 below, a copper-catalyzed coupling reaction will be used as the key step in the scale-up preparations of A11. Thus, after the key intermediate vinyl iodide 5 is synthesized (in four steps from commercially available dimethoxybenzyl alcohol 1), it may be coupled with commercially available 2-methylphenol to yield vinyl ether 6. Deprotection of 6 should then proceed cleanly to provide A11 in reasonable yields. Subsequent purifications will allow us to safely use this compounds as a potential skin lightening agent.

Scheme 1. Scheme for the Preparation of A11:
2-Methylphenyl-E-(3-hydroxy-5-methoxy)-styryl ether A more generalized scheme for the preparation of A11 and other analogs, is shown below in Scheme 2.

Scheme 2.
General Scheme for the O-vinylation of phenol or Substituted phenols by Reaction with 1-(E)-(3-hydroxy-5methoxy)-styryliodide, 10

13, R₁ = CH₃, R₂ = R₃ = H, R₄ = H, X = O, 52%
14, R₁ = R₃ = H, R₂ = CH₃, R₄ = H, X = O, 56%
15, R₁ = R₂ = H, R₃ = CH₃, R₄ = H, X = O, 51%
16, R₁ = R₃ = H, R₂ = OMe, R₄ = H, X = O, 50%
17, R₁ = R₂ = H, R₃ = OMe, R₄ = H, X = O, 49%

(Percentages are overall yelds from 10 to ether)

2-Methylphenyl-E-(3-hydroxy-5-methoxy)-styryl ether (13)

The coupling of o-cresol (0.09 mL, 94.08 mg, 0.87 mmol) and vinyl iodide 12 (300 mg, 0.58 mmol) was carried out according to general procedure B. The crude oil was purified by FCC on silica gel (3% ethylacetate in hexane) to afford ether 13 and the silylvinylether intermediate of 13. The reaction of the silylvinyl ether intermediate 13 (49 mg, 0.01 mmol) with TBAF-THF (1.0 M, 0.12 mL, 1.1 eq) in THF (3 mL) gave the crude oil of 13, according to the general procedure C. The crude oil was purified by FCC on silica gel (7% ethyl acetate in hexane) and afforded pure vinyl ether 13; overall yield of ether 13 from 12 (76 mg, 52%): $^1$H NMR (300 MHz, CDCl$_3$) δ 7.24-7.14 (3H, m, HAr & HC═), 7.06-6.99 (2H, m, HAr), 6.44 (1H, t, J=1.2 Hz, HAr), 6.39 (1H, t, J=1.2 Hz, HAr), 6.28 (1H, t, J=2.1 Hz, HAr), 6.15 (1H, d, J=12.6 Hz, HC═), 4.81 (1H, br, s, HC—), 3.80 (3H, s, H$_3$CO), 2.31 (3H, s, H$_3$C); $^{13}$C NMR (75 MHz, CDCl$_3$) δ 160.9, 156.8, 156.5, 145.0, 144.1 137.6, 131.2, 127.0, 123.5, 116.6, 111.9, 104.9, 103.9, 99.6, 55.2, 15.9.

3-Methylphenyl-E-(3-hydroxy-5-methoxy)-styryl ether (14)

The coupling of m-cresol (94.08 mg, 0.87 mmol) with vinyl iodide 12 (300 mg, 0.58 mmol) was carried out according to general procedure B. The crude oil was purified by FCC on silica gel (5% ethyl acetate in hexane) to afford vinyl ether 14 and the silylvinyl ether intermediate of 14. The reaction of the silylvinyl ether intermediate of 14 (51 mg, 0.01 mmol) with TBAF.THF (1.0 M, 0.12 mL, 1.1 eq) in THF (3 mL) gave the crude oil of vinyl ether 14, according to general procedure C. The crude oil was purified by FCC on silica gel (5% ethyl acetate in hexane) to afford pure vinyl ether 14; overall yield of vinyl ether 14 from 12 (84 mg, 56%): $^1$H NMR (300 MHz, CDCl$_3$) δ 7.28-7.14 (2H, m, HAr & HC═), 6.96-6.87 (3H, m, HAr), 6.47 (1H, t, J=1.2 Hz, HAr), 6.42 (1H, t, J=1.2 Hz, HAr), 6.30 (1H, t, J=2.1 Hz, HAr), 6.24 (1H, d, J=12.3 Hz, HC═), 4.93 (1H, br, s, HO—), 3.81 (3H, s, H$_3$CO), 2.38 (3H, s, H$_3$C); $^{13}$C NMR (75 MHz, CDCl$_3$) δ 161.0, 156.8, 156.7, 144.2, 139.9, 137.5, 129.4, 124.1, 117.6, 113.9, 112.8, 105.0, 104.1, 99.7, 55.2, 21.3; LRMS (EI), m/z (relative intensity): 256 [M]$^+$, 241, 91, 77, 63.

4-Methylphenyl-E-(3-hydroxy-5-methoxy)-styryl ether (15)

The coupling of p-cresol (94.08 mg, 0.87 mmol) with vinyl iodide 12 (300 mg, 0.58 mmol) was carried out according to general procedure B. The crude oil was purified by FCC on silica gel (3% ethylacetate in hexane) to afford vinyl ether 15 and the silylvinyl ether intermediate of 15. The reaction of the silylvinyl ether intermediate of 15 (48 mg, 0.01 mmol) with TBAF.THF (1.0 M, 0.12 mL, 1.1 eq) in THF (3 mL) gave the crude oil of vinyl ether 15, according to the general procedure C. The crude ether was purified by FCC on silica gel (7% ethyl acetate in hexane) to afford vinyl ether 15; overall yield of vinyl ether 15 from 12 (75 mg, 51%): $^1$H NMR (300 MHz, CDCl$_3$) δ 7.18-7.12 (3H, m, HAr & HC═), 6.98-6.95 (2H, m, HAr), 6.45 (1H, t, J=1.2 Hz, HAr), 6.41 (1H, t, J=1.2 Hz, HAr), 6.29 (1H, t, J=2.1 Hz, HAr), 6.21 (1H, d, J=12.3 Hz, HC═), 5.21 (1H, br, 5, HC—), 3.79 (3H, s, H$_3$CO), 2.35 (3H, s, H$_3$C); $^{13}$C NMR (75 MHz, CDCl$_3$) δ 161.0, 156.8, 144.6, 137.5, 135.4, 132.8, 130.1, 116.9, 112.5, 105.0, 104.0, 99.7, 55.2, 20.6; LRMS (EI), m/z (relative intensity): 256 [M]$^+$, 241, 91, 77, 65.

3-Methoxyphenyl-E-(3-hydroxy-5-methoxy)-styryl ether (16)

The coupling of m-anisole (0.094 mL, 108.5 mg, 0.87 mmol) with vinyl iodide 12 (300 mg, 0.58 mmol) was carried out according to general procedure B. The crude oil was purified by FCC on silica gel (2% ethylacetate in hexane) to afford vinyl ether 16 and silylvinyl ether intermediate 16i. The reaction of the silylvinyl ether intermediate 16i (112 mg, 0.22 mmol) with TBAF.THF (1.0 M, 0.24 mL, 1.1 eq) in THF (3 mL) gave the crude oil of vinyl ether 16, according to the general procedure C. The crude oil was purified by FCC on silica gel (2% ethyl acetate in hexane) to afford vinyl ether 16; overall yield of vinyl ether 16 from 12 (79.5 mg, 50%). 16i: $^1$H NMR (300 MHz, CDCl$_3$) δ 7.78-7.74 (4H, m, HAr), 7.45-7.37 (6H, m, HAr), 7.28-6.26 (1H, m, HAr), 6.88 (1H, d, J=12.3 Hz, HC═), 6.69-6.57 (3H, n, HAr), 6.39 (1H, t, J=1.2 Hz, HAr), 6.35, (1H, t, J=1.2 Hz, HAr), 6.22 (1H, t, J=2.1 Hz, HAr), 6.15 (1H, d, J=12.3 Hz, HC═), 3.83 (3H, s, H$_3$CO), 3.60 (3H, s, H$_3$CO); $^{13}$C NMR (75 MHz, CDCl$_3$). δ 160.8, 160.5, 158.1, 156.8, 143.4, 134.9, 132.9, 129.8, 127.7, 113.4, 109.3, 108.9, 108.8, 104.9, 104.0, 103.0, 55.3, 55.0; LRMS (EI), m/z (relative intensity): 511 [M]$^+$, 454, 305 (100), 227, 77. 16: $^1$H NMR (300 MHz, CDCl$_3$) δ 7.29-7.26 (1H, m, HAr), 7.15 (1H, d, J=12.3 Hz, HC═), 6.70-6.62 (3H, m, HAr), 6.46 (1H, t, J=1.2 Hz, HAr), 6.41 (1H, t, J=1.2 Hz, HAr), 6.30 (1H, t, J=2.1 Hz, HAr), 6.25 (1H, d, J=12.3 Hz, HC═), 5.05 (1H, br, s, HC—), 3.83 (3H, s, H$_3$CO), 3.30 (3H, s, H$_3$CO); $^{13}$C NMR (75 MHz, CDCl$_3$) δ 161.0, 160.8, 158.1, 156.8, 143.8, 137.3, 130.1, 113.3, 109.0, 105.1, 104.1, 103.1, 99.9, 55.3, 55.2; LRMS (EI), m/z (relative intensity): 272 [M]$^+$, 255, 92, 77, 64.

4-Methoxyphenyl-E-(3-hydroxy-5methoxy)-styryl ether (17)

The coupling of p-anisole (108.5 mg, 0.87 mmol) with vinyl iodide 12 (300 mg, 0.58 mmol) was carried out according to general procedure B. The crude oil was purified by FCC on silica gel (2% ethylacetate in hexane) to afford vinyl ether 17 and the silylvinyl ether intermediate of 17. The reaction of the silylvinyl intermediate of 17 (111 mg, 0.22 mmol) with TBAF.THF (1.0 M, 0.24 mL, 1.1 eq) in THF (3 mL) gave the crude oil of vinyl ether 17, according to the general procedure C. The crude oil was purified by FCC on silica gel (2% ethyl acetate in hexane) to afford pure vinyl ether 17; overall yield of vinyl ether 17 from 12 (77.8 mg, 49%): $^1$H NMR (300 MHz, CDCl$_3$) δ 7.10 (1H, d, J=12.3 Hz, HC=), 7.03-7.00 (2H, m, HAr), 6.91-6.88 (2H, m, HAr), 6.43 (1H, t, J=1.2 Hz, HAr), 6.39 (1H, t, J=1.2 Hz, HAr), 6.28 (1H, t, J=2.1 Hz, HAr), 6.15 (1H, d, J=12.3 Hz, HC=), 5.17 (1H, br, s, HC—), 3.82 (3H, s, H$_3$CO), 3.79 (3H, s, H$_3$CO); $^{13}$C NMR (75 MHz, CDCl$_3$) δ 161.0, 156.7, 155.7, 150.8, 145.4, 137.6, 118.4, 114.7, 111.9, 104.9, 103.9, 99.6, 55.6, 55.2; LRMS (EI), m/z (relative intensity): 272 [M]$^+$, 255, 134, 109, 77.

APPENDIX

The information contained in the attached Appendix is expressly incorporated by reference herein in its entirety.

REFERENCES WHICH ARE EXPRESSLY INCORPORATED BY REFERENCE HEREIN IN THEIR ENTIRETY

1. Asianscientist: http://www.asianscientist.com/features/skin-whitening-products-asia-2012/
2. Choi, T-Y., Kim, J-H., Ko, D. H., Kim, C-H., Hwang, J-S., Ahn, S., Kim, S. Y., Kim, C-D., Lee, J H., and Yoon, T-J. (2007). Zebrafish as a new model for phenotype-based screening for melanogenic regulatory compounds. Pigment Cell Res. 20; 120-127.
3. Kanebo (2013): http://www.kanebo.com/pressroom/pressrelease/20130723.pdf
4. Kabir, M. S., Engelbrecht, K., Polanowski, R., Rott, M. A., Schwan, W. R., Stemper, M., Reed, K., Sherman, D., Cook, J. M., Monte, A., (2008). New class of gram-positive antibacterials: Inhibitors of MRSA and surrogates of the causative agents of anthrax and tuberculosis. Bioorg. Med. Chem. Lett. 18: 5745-5749.
5. Rodriguez, R., Haugen, R., Rueber, A., and Huang, C-C. (2014). Reversible neuronal and mucular toxicity of caffeine in developing vertebrates. Comp. Biochem. Physiol. Part C (in press).
6. Santoriello, C. Gennaro, E., Anelli, V., Distel, M., Kelly, a., Koster, R. W., Hurlstone, A., and Mione, M. (2010). Kita driven expression of oncogenic HRAS leads to early onset and highly penetrant melanoma in zebrafish. PLoS ONE 5(12):e15170.
7. Smit, N., Vicanova, J., and Pavel, S. (2009). The hunt for natural skin whitening agents. Int. J. Mol. Sci. 10:5326-5349.

Various other embodiments of the present invention are contemplated as being within the scope of the filed claims particularly pointing out and distinctly claiming the subject matter regarded as the invention.

The invention claimed is:

1. A method of inhibiting melanin synthesis and/or removing existing pigmentation from skin, said method comprising the step of administering an effective amount of a compound having the following formula:

2. A method of inhibiting melanin synthesis and/or removing existing pigmentation from skin, said method comprising the step of administering an effective amount of a compound having the following formula:

3. A method of inhibiting melanin synthesis and/or removing existing pigmentation from skin, said method comprising the step of administering an effective amount of a compound having the following formula:

4. A method of inhibiting melanin synthesis and/or removing existing pigmentation from skin, said method comprising the step of administering an effective amount of a compound having the following formula:

5. A method of inhibiting melanin synthesis and/or removing existing pigmentation from skin, said method comprising the step of administering an effective amount of a compound having the following formula:

* * * * *